US007857815B2

(12) United States Patent
Zucherman et al.

(10) Patent No.: US 7,857,815 B2
(45) Date of Patent: *Dec. 28, 2010

(54) SYSTEM AND METHOD FOR STRENGTHENING A SPINOUS PROCESS

(75) Inventors: James F. Zucherman, San Francisco, CA (US); Ken Y. Hsu, San Francisco, CA (US); Steven T. Mitchell, Pleasant Hill, CA (US)

(73) Assignee: Kyphon SARL, Neuchatel (CH)

( * ) Notice: Subject to any disclaimer, the term of this patent is extended or adjusted under 35 U.S.C. 154(b) by 892 days.

This patent is subject to a terminal disclaimer.

(21) Appl. No.: 11/737,676

(22) Filed: Apr. 19, 2007

(65) Prior Publication Data

US 2008/0027434 A1 Jan. 31, 2008

Related U.S. Application Data

(60) Provisional application No. 60/816,117, filed on Jun. 22, 2006, provisional application No. 60/853,962, filed on Oct. 24, 2006.

(51) Int. Cl.
*A61B 17/58* (2006.01)
(52) U.S. Cl. ...................................... 606/86 A; 606/92
(58) Field of Classification Search .................. 606/96, 606/94, 86 A, 251, 250, 90, 151, 99, 92, 426, 606/254; 128/898
See application file for complete search history.

(56) References Cited

U.S. PATENT DOCUMENTS

| 887,103 | A | 5/1908 | Lane |
|---|---|---|---|
| 2,416,228 | A | 2/1947 | Sheppard |
| 2,757,665 | A | 8/1956 | Tanikawa |
| 3,906,957 | A | 9/1975 | Weston |
| 4,246,895 | A | 1/1981 | Rehder |
| 4,896,663 | A | 1/1990 | Vandewalls |
| 5,464,413 | A | 11/1995 | Siska, Jr. et al. |
| 5,674,221 | A * | 10/1997 | Hein et al. .................... 606/54 |
| 6,048,346 | A | 4/2000 | Reiley et al. |
| 6,066,102 | A | 5/2000 | Townsend et al. |
| 6,277,123 | B1 | 8/2001 | Maroney et al. |
| 6,436,117 | B1 | 8/2002 | Waller et al. |
| 6,676,664 | B1 | 1/2004 | Al-Assir |
| 6,773,437 | B2 * | 8/2004 | Ogilvie et al. ................. 606/75 |
| 7,611,526 | B2 | 11/2009 | Carl et al. |
| 7,708,765 | B2 * | 5/2010 | Carl et al. .................... 606/279 |

OTHER PUBLICATIONS

European Patent Office, "Notification of Transmittal of the International Search Report and The Written Opinion of the International Searching Authority, or the Declaration," for PCT/US07/67789, mailed Jun. 26, 2008, 7 pages.

* cited by examiner

*Primary Examiner*—Pedro Philogene
(74) *Attorney, Agent, or Firm*—Haynes and Boone LLP

(57) ABSTRACT

A system and method for repairing or reinforcing the spinous process. The system and method provide a procedure and surgical tools for injecting a flowable bone repair material into and optionally around the spinous process. The system and method include location of the guide over the spinous process, preparation of the spinous process for injection and injection of a flowable material into the spinous process. The system and method reinforce the spinous process, increasing the strength of the spinous process and enhancing the applicability and outcome of other surgical spinal interventions.

28 Claims, 15 Drawing Sheets

US 7,857,815 B2

SYSTEM AND METHOD FOR STRENGTHENING A SPINOUS PROCESS

CLAIM OF PRIORITY

This U.S. Patent Application claims priority from U.S. Provisional Patent Application No. 60/816,117, filed Jun. 22, 2006 and U.S. Provisional Patent Application No. 60/853,962, filed Oct. 24, 2006, both of which are incorporated herein by reference.

BACKGROUND OF INVENTION

The spinal column has many functions including supporting the body, weight transfer and motion, and protection of the spinal cord and the nerve roots. The spinal column is a structure composed primarily of bones, ligaments, muscles, and cartilage. The bones of the spinal column are called vertebrae.

Normal healthy bone is composed of a framework made of proteins, collagen and calcium salts. Healthy bone is typically strong enough to withstand the various stresses experienced by an individual during his or her normal daily activities, and can normally withstand much greater stresses for varying lengths of time before failing. However, osteoporosis or a host of other diseases can affect and significantly weaken healthy bone over time. In osteoporosis, for example, bone mineral density is reduced over time leading to greater likelihood of fracture. If unchecked, such factors can degrade bone strength to a point where the bone is especially prone to fracture, collapse and/or is unable to withstand even normal daily stresses.

As the population ages, it is anticipated that there will be an increase in adverse spinal conditions which are characteristic of weakened bone. Also, with aging come increases in spinal stenosis, which is characterized by thickening of the bones, which make up the spinal column and facet arthropathy. These degenerative conditions as well as physical trauma can lead to failure or instability of the spinal column. Damage to the spinal column often leads to pain and difficulties with mobility. Accordingly, there have been developed surgical procedures and implants for alleviating conditions such as spinal stenosis, vertebral fracture and other spinal injury.

Many surgical interventions, depend upon implanting components relative to the spinous process of the vertebra. For example, U.S. Pat. No. 6,669,842 to Zucherman et al. titled, "Spine Distraction Implant," describes, "An implant that is implanted between adjacent spinous processes for the relief of pain associated with the spine. The device 101, illustrated in FIG. 1, has a spacer to distract apart the adjacent spinous processes 102, 103." This device can be used to ease the pain associated with spinal stenosis. Other interventions implant components that rely for their operation upon interaction with the spinous process. However, the strength of the spinous process may have been compromised by the degenerative processes described above.

In view of the need for a strong spinous process, it would therefore be desirable to have a procedure for enhancing the strength of a spinous process of a patient.

It would also be desirable to have a minimally invasive procedure for enhancing the strength of a spinous process of a patient.

It would further be desirable to have a procedure for enhancing the strength of a spinous process of a patient that could be performed in conjunction with a surgical intervention that affects the spinous process.

It would still further be desirable to provide tools and instruments to facilitate a procedure for enhancing the strength of a spinous process of a patient.

BRIEF DESCRIPTION OF THE DRAWINGS

Further features of the invention, its nature and various advantages will be more apparent from the accompanying drawings and the following detailed description of the preferred embodiments, in which.

DETAILED DESCRIPTION OF THE INVENTION

Figure 1:
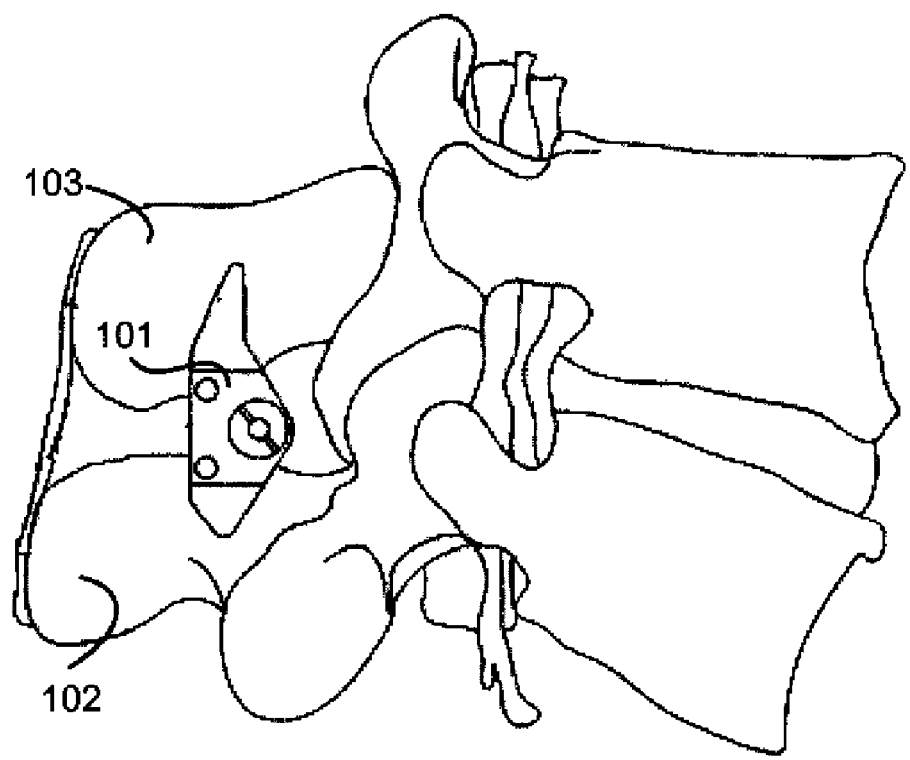
FIG. 1 shows a surgical implant in position between adjacent spinous processes.

In view of the foregoing background of the invention, it is an object of the present invention to provide a procedure for enhancing the strength of a spinous process of a patient.

It is also an object of the present invention to provide a minimally invasive procedure for enhancing the strength of a spinous process of a patient.

It is a further object of the present invention to provide a procedure for enhancing the strength of a spinous process of a patient that may be performed in conjunction with a surgical intervention that affects the spinous process.

It is still further an object of the present invention to provide tools and instruments to facilitate a procedure for enhancing the strength of a spinous process of a patient.

These and other objects of the present invention are accomplished by injecting a flowable reinforcing bone-filler material, such as polymethylmethacrylate (PMMA—commonly known as bone cement), into a fractured, weak, or diseased spinous process and lamina. Shortly after injection, the liquid bone filler material hardens or polymerizes, desirably supporting the spinous process and lamina internally. The procedure may make use of a guide element and corresponding tools to assist and control the injection of the flowable bone filler into and optionally around the spinous process.

In a general embodiment of the present invention, an insertion device, such as a needle, is inserted into a targeted spinous process using a guide to control the positioning of the needle and the depth of insertion. Bone filler such as bone cement is injected through the needle into the spinous process. Bone filler introduction is halted and the needle is retracted as a desired fill amount is reached. The bone filler is then allowed to harden.

In an alternative embodiment of the present invention, a cavity-forming device is inserted into the spinous process prior to injection of the bone filler. The cavity-forming device desirably compresses cancellous bone inside the spinous process forming a small cavity within the bone. The cavity-forming device is removed and bone filler is introduced through a needle or other injection tool. The cavity-forming device allows for easier insertion of the injection needle. Additionally, the creation of desired flow paths by the cavity-forming device permits greater control in the placement of the bone filler material within the spinous process and lamina. In addition, because a cavity is created within the spinous process prior to bone filler injection, lower pressures can be used allowing greater control of bone filler injection.

In an alternative embodiment of the present invention, one or more sealing elements are used in conjunction with injection of the bone filler. These sealing elements are applied around the spinous process and act to limit and control flow of bone filler during injection into the spinous process.

Other objects, advantages, and embodiments of the invention are set forth in part in the description which follows, and in part, will be obvious from this description, or may be learned from the practice of the invention.

Figure 2:
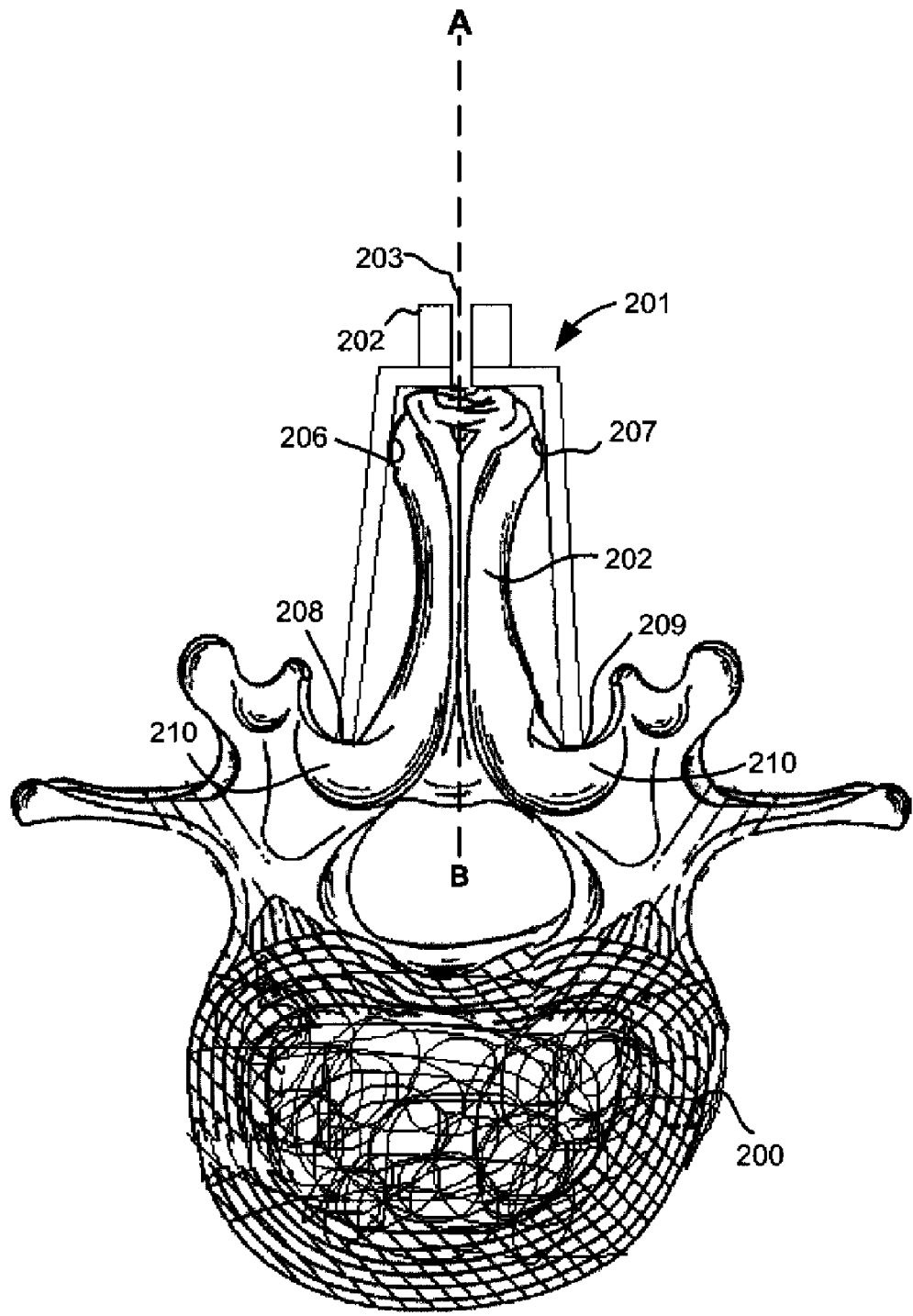
FIG. 2 shows a sectional view of a guide in accordance with one embodiment of the invention engaged with the spinous process of a vertebra.

FIG. 2 shows a guide 201 engaged with a spinous process 202 of a vertebra 200. Guide 201 defines a bore or guide bore 203. Bore 203 is aligned with the center of the spinous process and the axis of bore 203 is aligned with the axis of the spinous process, A-B. Guide 201 comprises two spinous process engagement surfaces 206, 207 which engage the sides of the spinous process, thus centering bore 203 on the apex of spinous process 202. Guide 201 also has two lamina engagement surfaces 208 and 209 which are shown in contact with the lamina 210 of vertebra 200. The two lamina engagement surfaces 208 and 209, in engaging the lamina, prevent further motion of the guide along the axis from A-B.

Figure 3:
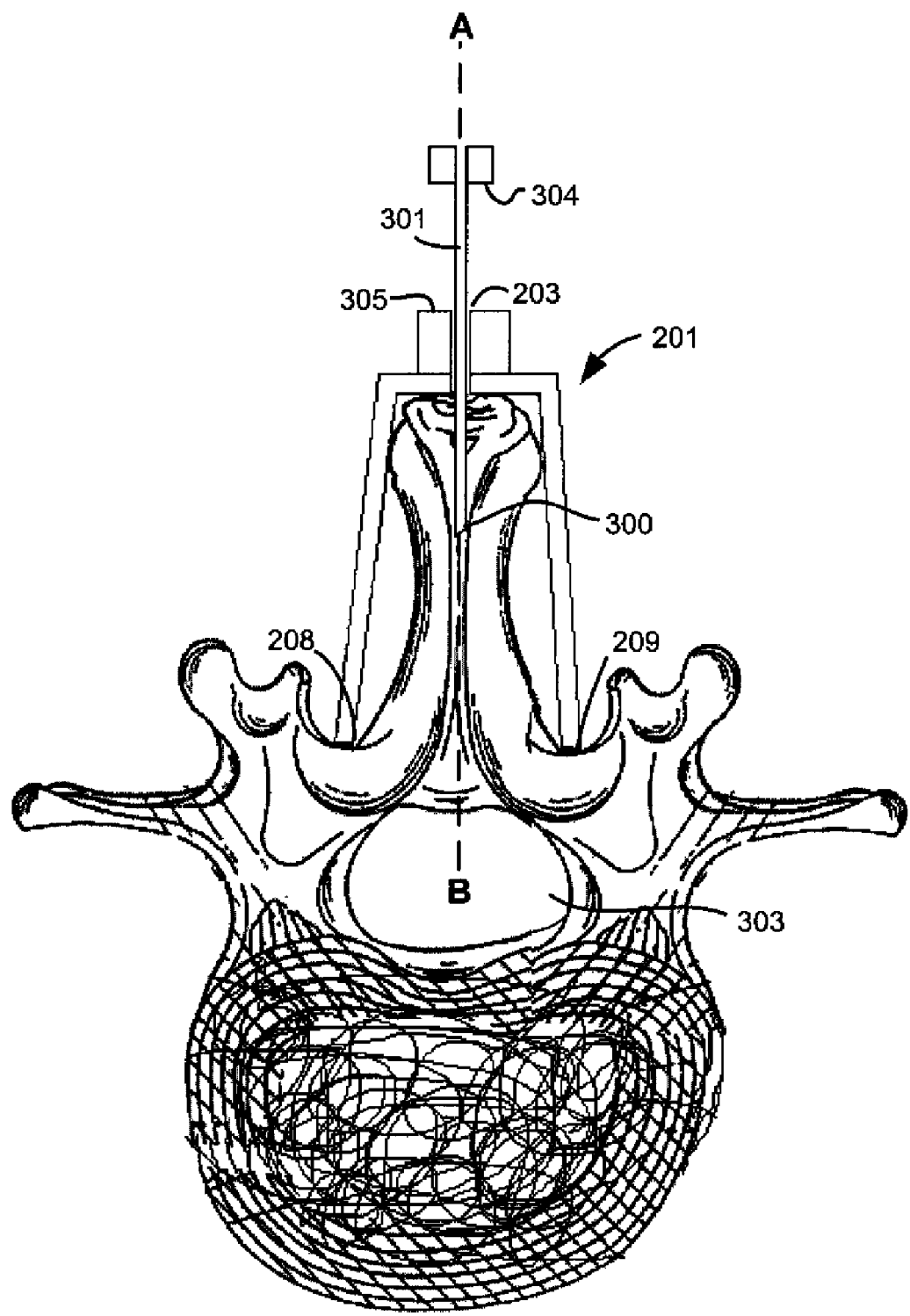
FIG. 3 shows a needle inserted through the guide of FIG. 2 into a spinous process.

As shown in FIG. 3, a needle 301 is inserted through bore 203 of guide 201 into spinous process 202. The guide bore 203 constrains the range of motion of needle 301 such that it can only be inserted along the axis A-B. Guide 201 thus ensures that needle 301 passes through the apex of the spinous process and along the axis of the spinous process.

Typically, needle 301 is introduced into spinous process 202 under X-ray control or a similar visualization system. The visualization system may also be used to determine proper placement of guide 201. Guide 201 may be made of metal and visible under X-ray. If guide 201 is made of plastic material, it may be impregnated with radio-opaque material or have radio-opaque markers applied to the guide surface in order to allow X-ray visualization.

During insertion, the physician must take care that needle 301 does not enter spinal canal 303. Thus, it is preferred that the needle be mechanically prevented from traveling along axis A-B prior to entering spinal canal 303. As shown in FIG. 3, needle 301 may include limit surface 304 which engages limit surface 305 of guide 201 to prevent further insertion of the needle along axis A-B. The distance from the tip 300 of the needle 301 to the limit surface of the needle measured along the axis of the needle is selected such that upon maximum insertion, tip 300 of needle 301 does not enter spinal canal 303. As shown in FIG. 3 the distance from lamina engagement surfaces 208 and 209 to the limit surface 305 of guide 201 measured along axis A-B controls the depth of insertion of tip 300 of needle 301. The needle will be inserted to a depth of from 50% to 95% of the distance from the apex of the spinous process to the wall of the spinal canal. Preferably, needle 301 and guide 201 are designed such that tip 300 of needle 201 at its maximal insertion is within the boundary area between the lamina and the spinous process.

Figure 4:
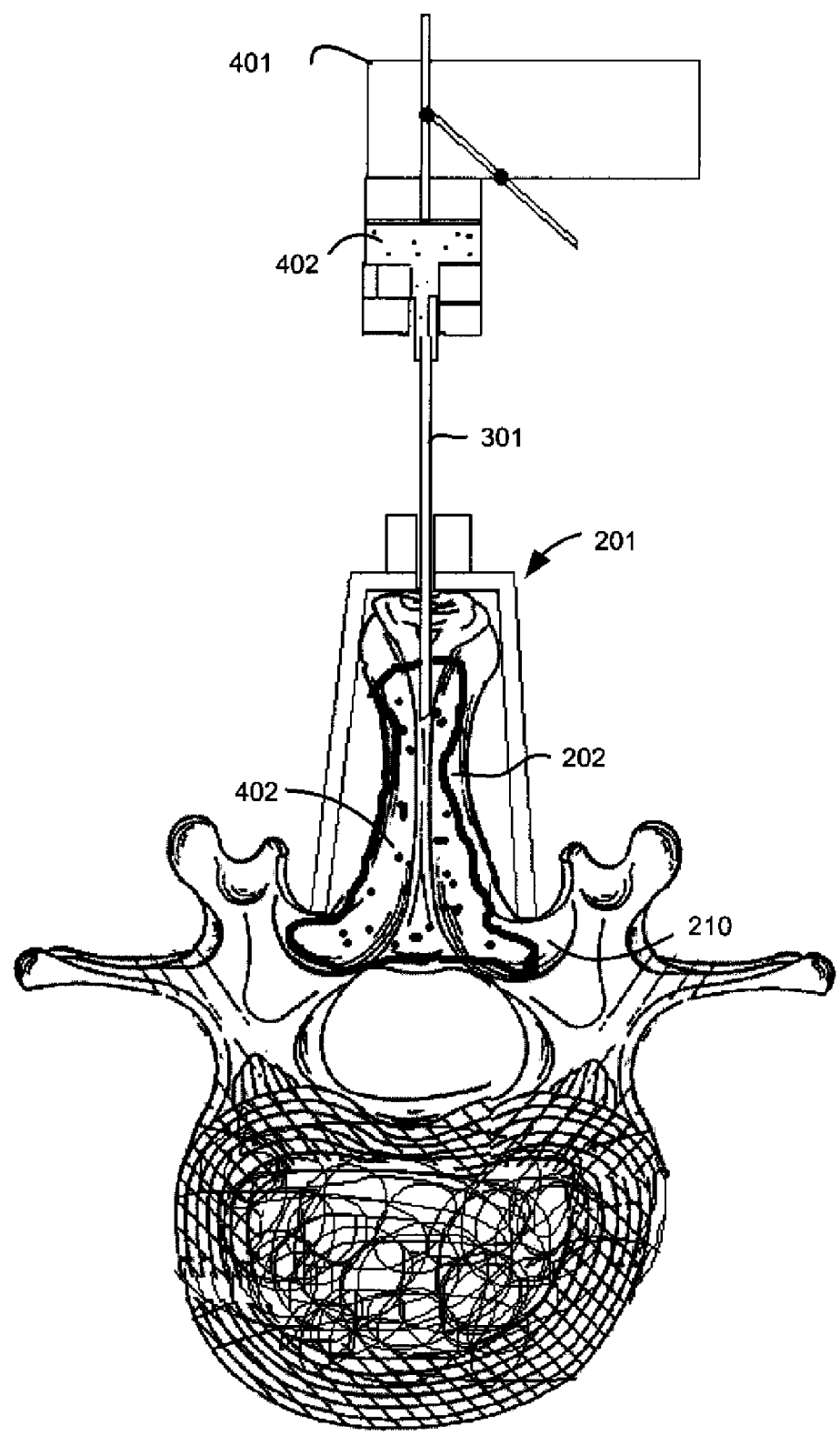
FIG. 4 shows flow of bone filler from an injector through a needle into the spinous process and lamina using the guide of FIG. 2.

As shown in FIG. 4, needle 301 is attached to bone cement injection device 401. Needle 301 may be provided with a threaded bore or similar coupling that mates with a bone cement injector for this purpose. The bone filler injection device may be a syringe or similar device. However, several companies offer purpose-made bone cement injection devices. A typical injection device has a pistol-shaped body, which supports a cartridge containing bone cement. The cement is typically in two-parts and must be mixed in a mixer and transferred into the cartridge for injection. Just after mixing, and prior to curing, the cement is in a flowing, viscous liquid state. The injection device has a ram, which is actuated by a manually movable trigger or screwing mechanism for pushing the viscous bone cement out the front of the cartridge through a suitable nozzle and into the interior of a bone. A suitable injection device is made by Stryker Corporation (Kalamazoo, Mich.) for example, This gun is manually operated though other types of injection device may be used including non-manual injection devices.

As shown in FIG. 4, injection device 401 forces bone cement 402 along needle 301 into spinous process 202. As also shown, the bone cement will flow into lamina 210. Needle 301 may be inserted or withdrawn from the spinous process along axis A-B during injection of bone cement such that bone cement is injected at different points in spinous process 202. This allows optimal impregnation of spinous process 202 with bone cement 402. In addition, the needle may be provided with one or more side ports instead of or in addition to the distal opening of the needle. The physician may monitor injection of the bone cement fluorospically or by direct visual observation if permitted by exposure of the spinous process. Additional systems for controlling flow of bone cement flowing are described in detail later.

Once injected into the spinous process, bone cement 402 undergoes a curing cycle of approximately 6 to 12 minutes. While curing, the cement passes from a viscous liquid to a hard rigid block. The bone cement must be injected and the needle withdrawn prior to hardening of the bone cement. After bone cement 402 has hardened, guide 201 may be removed from the spinous process. In order to reduce the possibility of guide 201 being stuck to spinous process 202, guide 201 may optionally be provided with a coating of a non-stick material such as TEFLON™ on any surface that comes in contact with the bone cement or spinous process. Alternatively, the portions of guide 201 that are exposed to the bone cement or spinous process, or indeed the entire guide, may be made from a non-stick plastic polymer such as TEFLON™.

Figure 5:
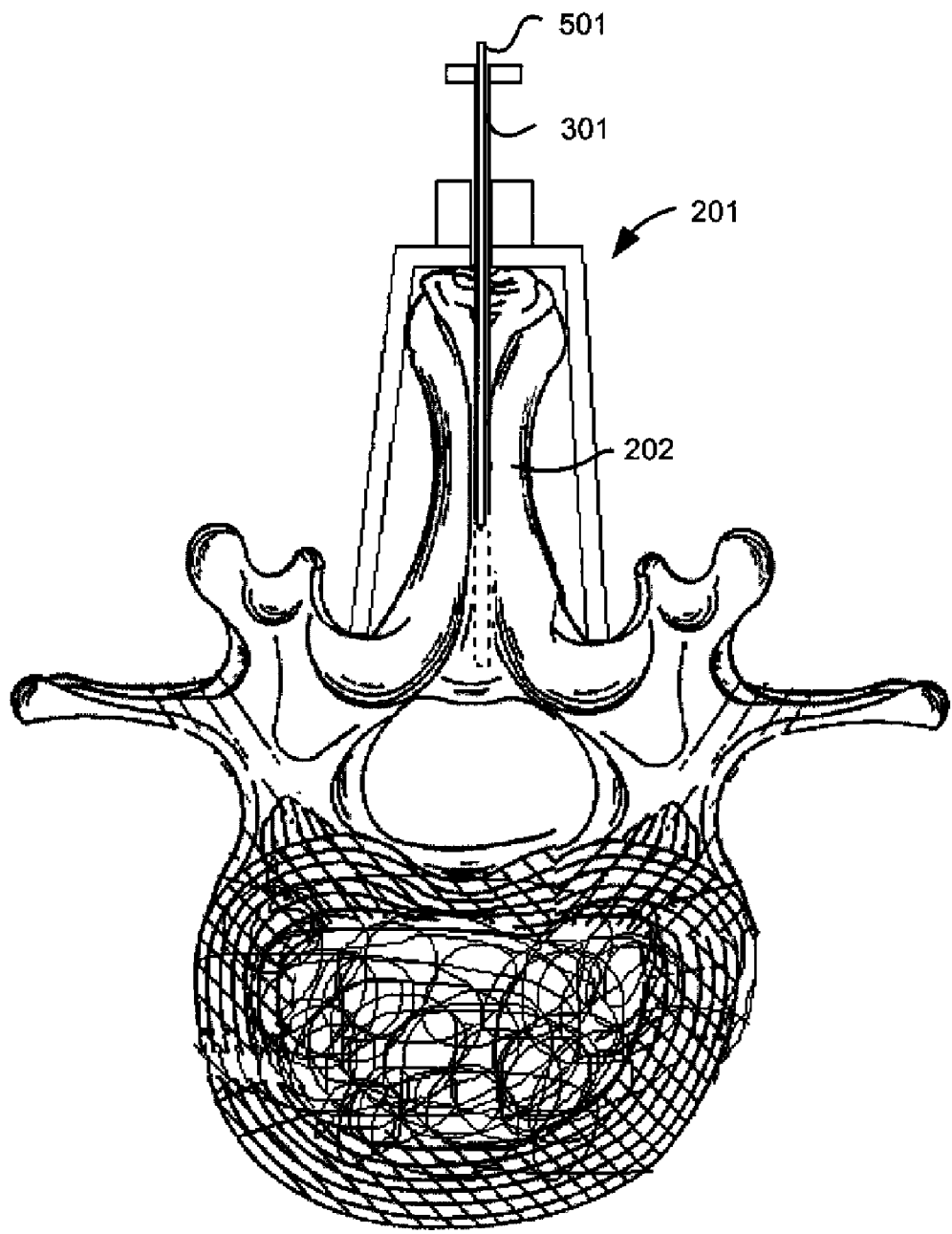
FIG. 5 shows introduction of a needle with a stylet through the guide of FIG. 2 into a spinous process.

FIG. 5 illustrates an alternative procedure in which, after placement of guide 201 over spinous process 202, a needle 301 is inserted as previously discussed. In order to facilitate introduction of needle 301, a stylet 501 is first inserted into needle 301. Stylet 501 strengthens needle 301 preventing damage to needle 301 during insertion and protecting the needle against obstruction. Stylet 501 may also be provided with a sharpened tip to aid insertion. Stylet 501 may also be provided with a limit surface (not shown) to prevent the stylet from being inserted more than a desired depth. After introduction of needle 301, stylet 501 is removed prior to connecting a bone cement injection device to needle 301.

Figure 6:
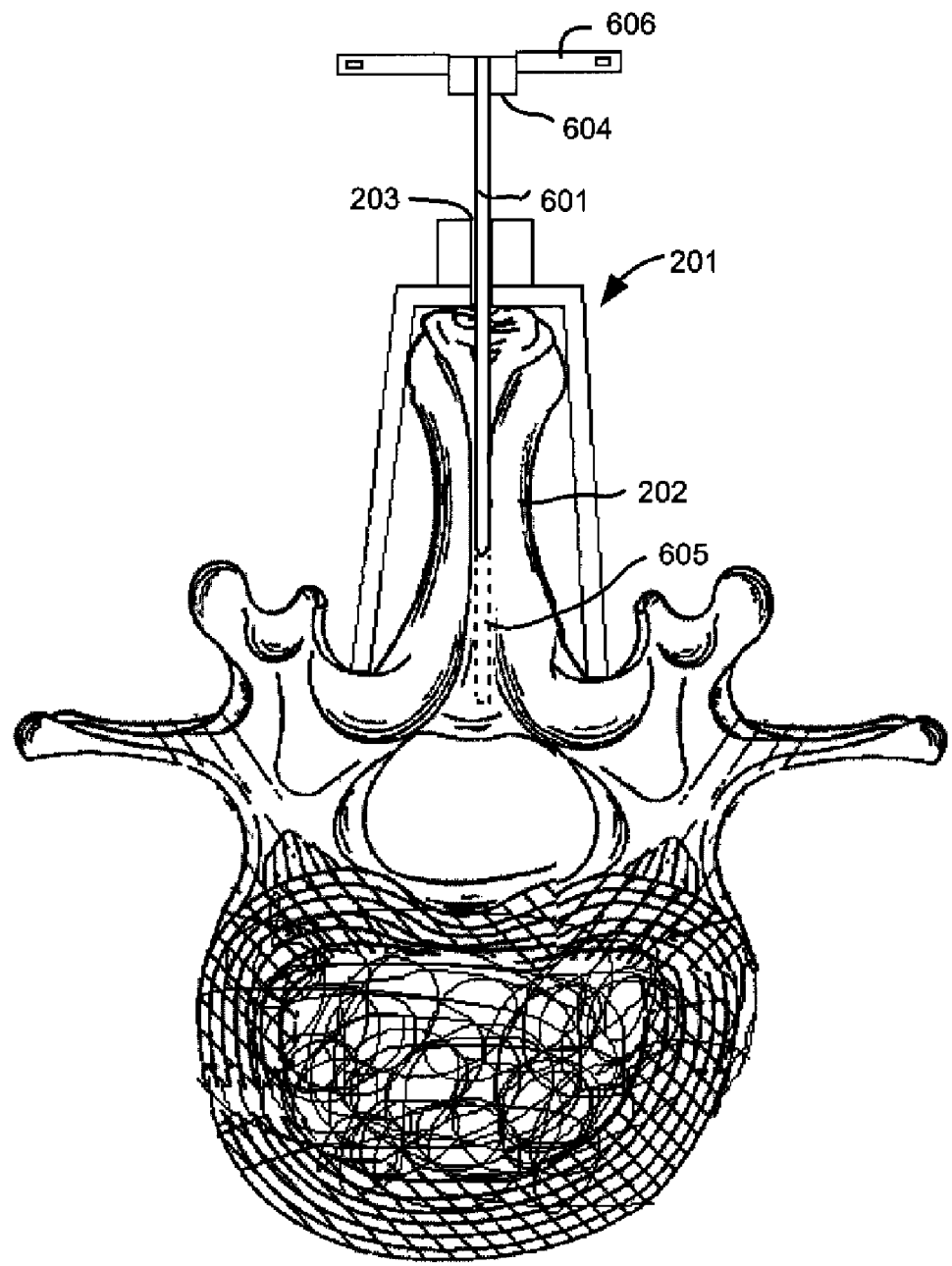
FIG. 6 shows introduction of a cavity-forming wire through the guide of FIG. 2 into a spinous process.

FIG. 6 illustrates an alternative procedure. In this procedure, after placement of glide 201 over spinous process 202, a solid wire 601 is introduced through bore 203 into the spinous process. Wire 601 may preferably be a Kirshner wire (K-wire) however similar tools such as drills, cannulae needles, awls, chisels and the like may be utilized to create the channel. In the embodiment illustrated in FIG. 6, wire 601 is provided with handle 606 for ease of insertion. Additionally limit surface 604 of handle 606 acts to limit take depth of insertion of wire 601 thus ensuring that the wire does not enter the spinal canal. After wire 601 has been inserted into spinous process 202 to the desired depth, wire 601 is withdrawn leaving channel 605 in the spinous process. After creation of channel 605, a needle is inserted for injection of bone cement as previously discussed. To facilitate the process, it is desirable that the wire has the same or a slightly larger diameter than the needle.

The use of the K-wire or similar tool as described above permits easier penetration of the needle and reduces the danger of the needle becoming damaged or clogged during introduction. In addition, the creation of desired flow path within the spinous process allows for better control of filler material within the spinous process. Furthermore, because a cavity is created within the spinous process prior to bone filler introduction, lower injection pressures can be used. The lower injection pressures also allow better control of bone filler injection. Other cavity-forming devices can be utilized to make or enlarge the cavity inside the spinous process before injection of bone cement. For example, a drill, wire brush or inflatable body may be used for this purpose.

In one alternative, a balloon may be inserted into the spinous process. The balloon is then inflated inside the spinous process compressing the cancellous bone of the interior against the cortical bone at the periphery of the spinous process. The balloon is inflated using a radio-opaque fluid and balloon inflation is monitored under fluoroscopic control. After inflation, the balloon is deflated and removed from the spinous process and the spinous process is filled with bone cement as before. This technique has the advantage of allowing easier injection of a greater amount of bone cement. In addition, by compressing the cancellous bone, this technique can be used to constrain the bone cement to the interior of the spinous process if this is desired.

Figure 7:
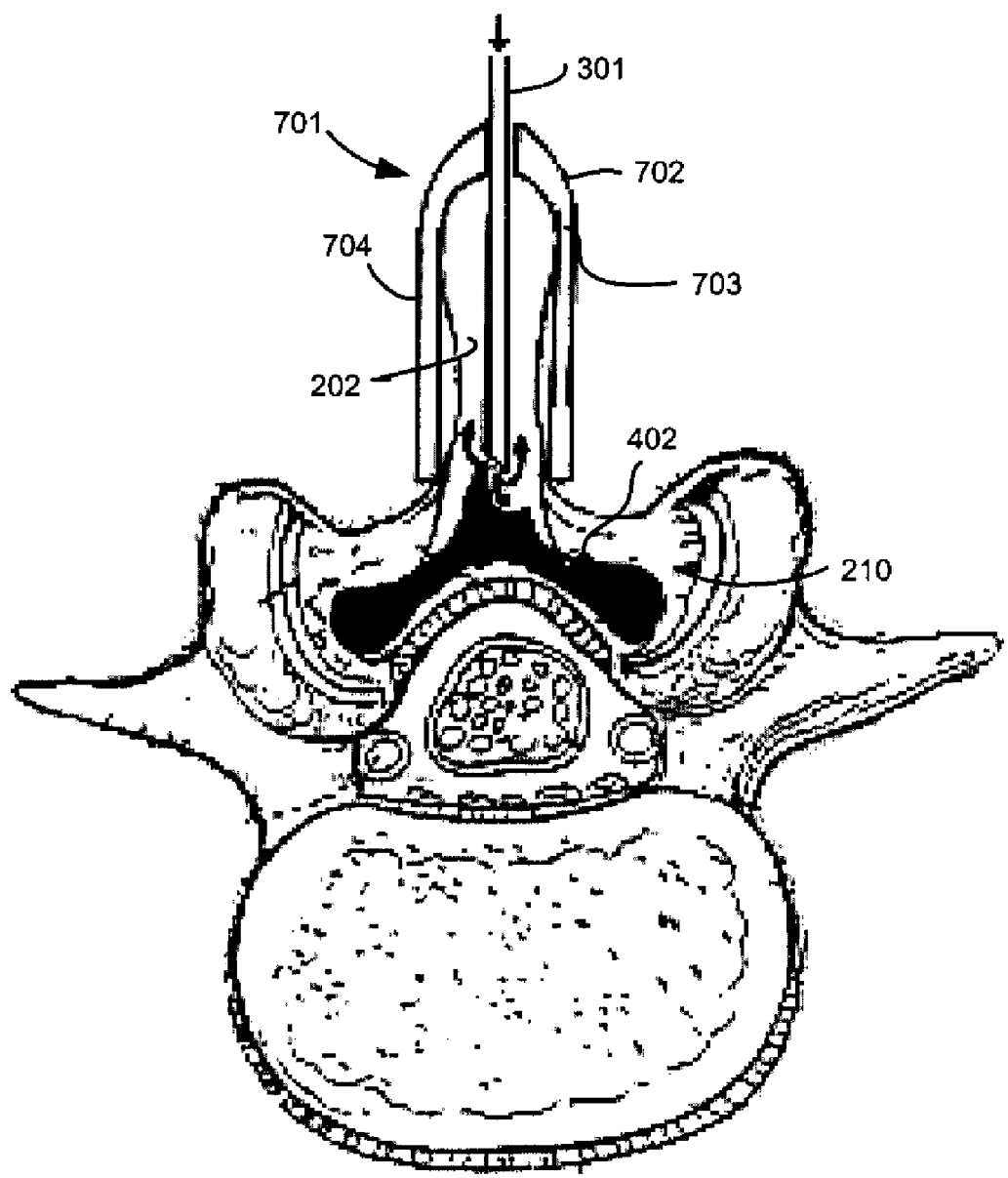
FIG. 7 shows a sectional view of a guide in accordance with one embodiment of the invention engaged with the spinous process of a vertebra as bone filler is injected into the spinous process and lamina.
Figure 8:
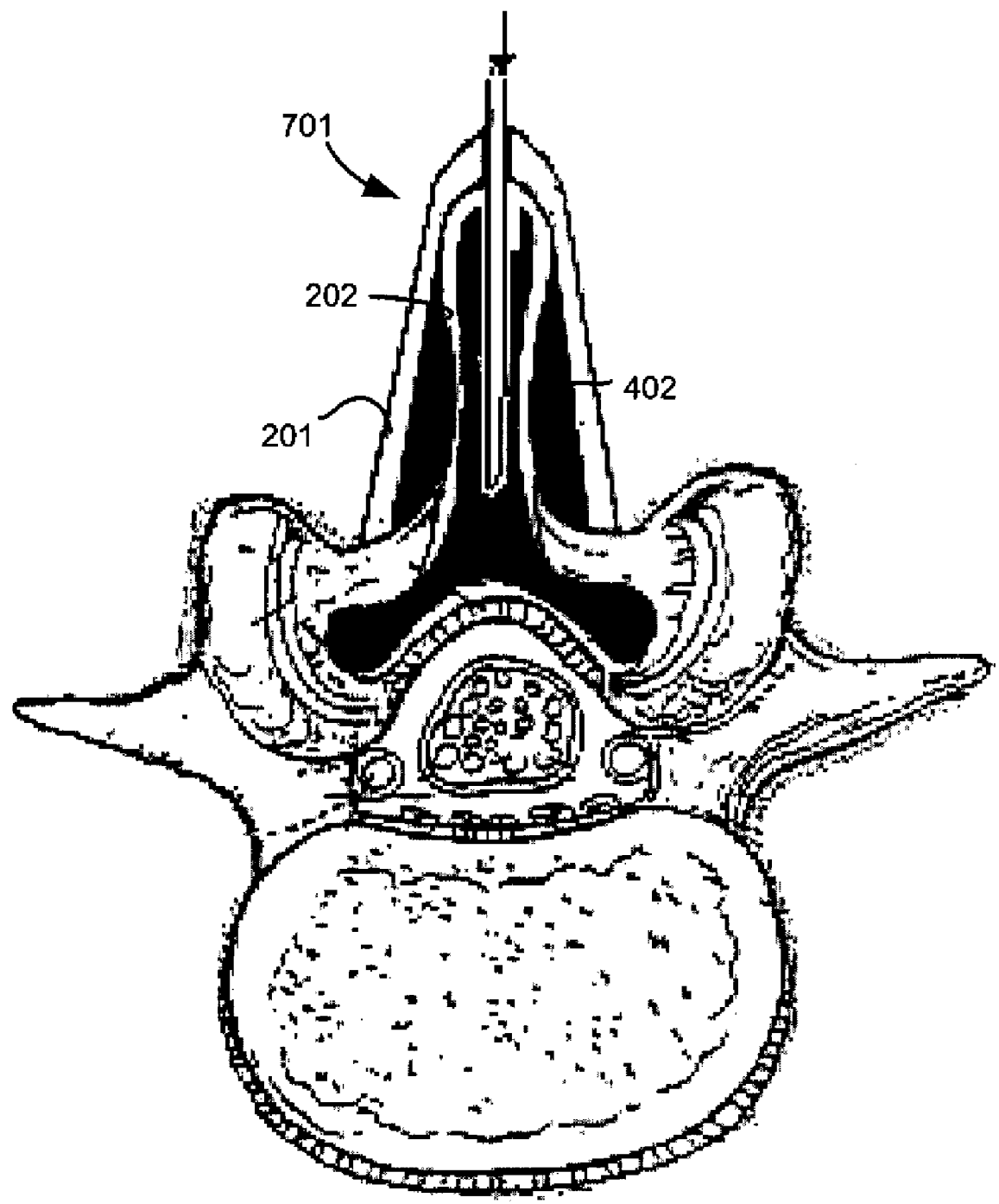
FIG. 8 shows a shows a sectional view of a guide in accordance with one embodiment of the invention engaged with the spinous process of a vertebra which has been impregnated and surrounded by bone filler.

FIG. 7 shows an alternative guide 701 having a connector 702 between arms 703, 704 Connector 702 conforms to the apex of spinous process 202. In addition, FIG. 7 illustrates the flow of bone cement 402 into lamina 210. In FIG. 8, a similar guide is shown at a later point in the injection of bone filler. As is shown in this example, bone filler 402 can optionally be allowed to fill the space between guide 201 and spinous process 202. Bone cement may seep through the bone to the space between the guide and the spinous process. Alternatively, holes may be provided in the spinous process to allow the cement to seep into the space between the bone and the spinous process. This additional bone filler serves to provide external support to the spinous process in addition to the internal support provided by impregnation of the spinous process.

Figure 9A:
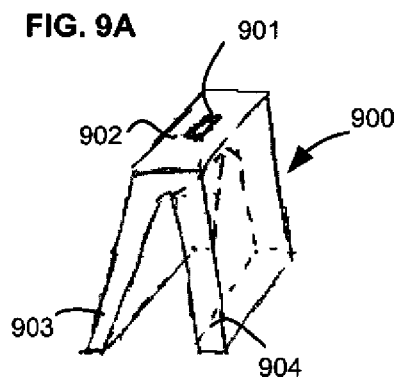
FIGS. 9A-9N show different embodiments of the guides of the present invention.
Figure 9B:
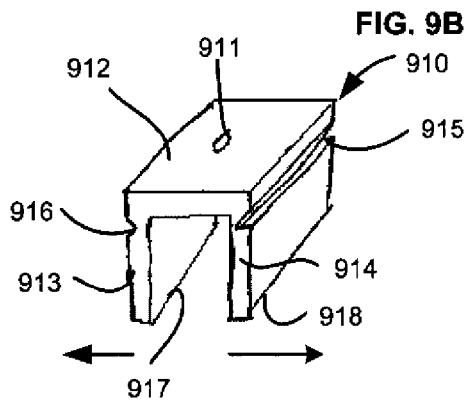
Figure 9C:
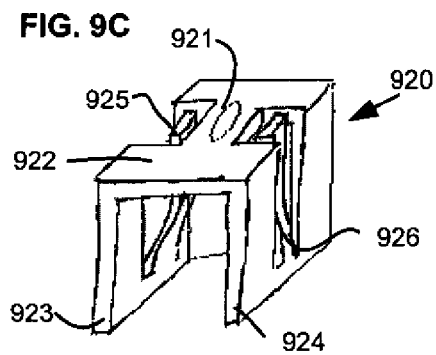
Figure 9D:
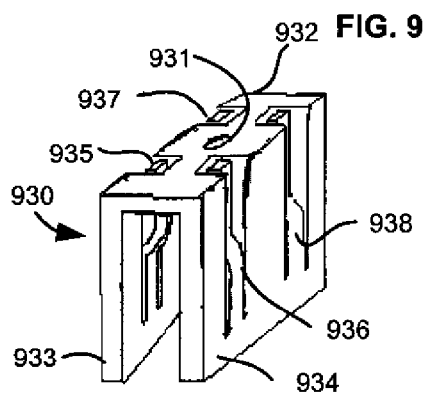
Figure 9E:
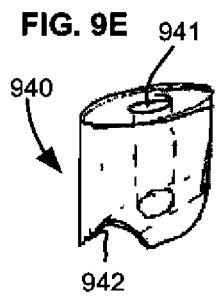
Figure 9F:
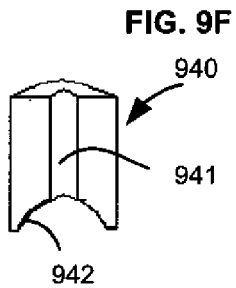
Figure 9G:
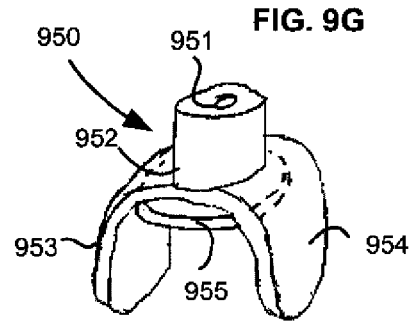
Figure 9H:
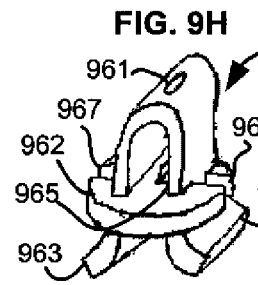
Figure 9I:
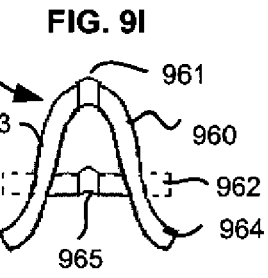
Figure 9J:
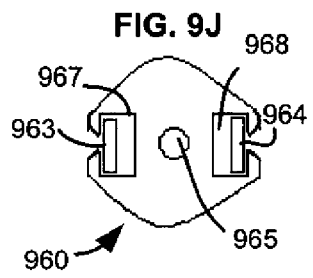
Figure 9L:
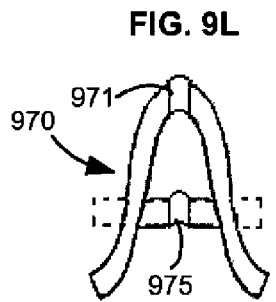
Figure 9K:
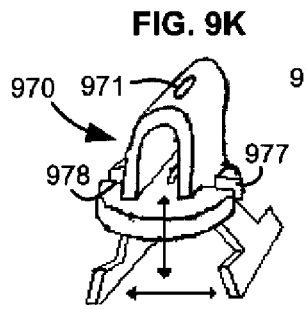
Figure 9M:
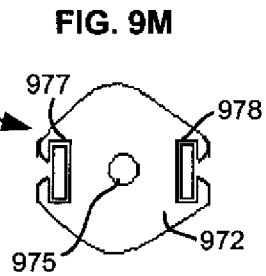
Figure 9N:
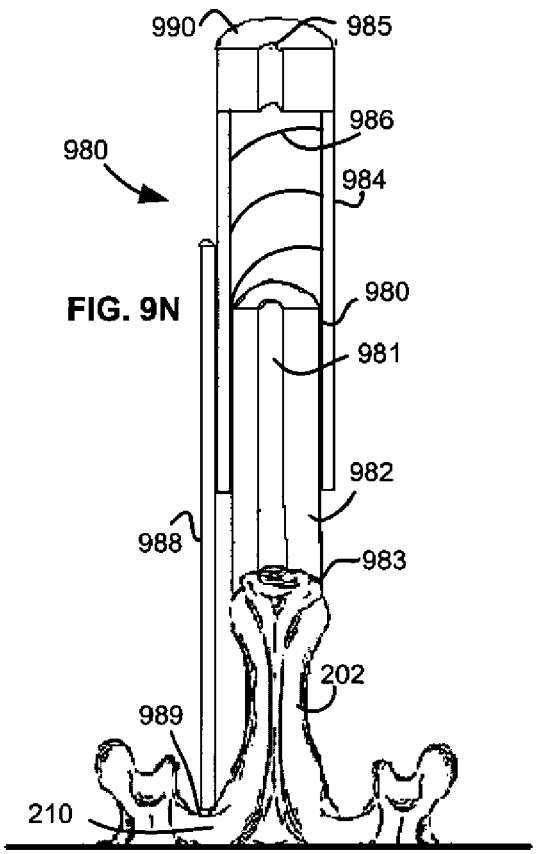

FIGS. 9A-N illustrate various embodiments of guides in accordance with the principles of this invention. FIG. 9A shows a V-shaped guide 900 having a bore 901 in connector section 902. Bore 901 acts as a position and direction guide for introduction of a needle or other surgical instrument. Guide 900 comprises two arms 903, 904 which engage the spinous process while centering bore 901 on the apex of the spinous process. Preferably, arms 903, 904 are sized such they contact the lamina on either side of a vetebra to be reinforced. In such case, bore 901 can serve both as an insertion point and direction guide and as a depth guide. In this embodiment, arms 903, 904 are formed in one piece with connector section 902 disposed between them. Guide 900 is preferably made of metal or plastic.

FIG. 9B shows a U-shaped guide 910 having a guide bore 911 in connector section 912. Bore 911 acts as a position and direction guide for introduction of a needle or other surgical instrument. Guide 910 comprises two arms 913, 914 which engage the spinous process while centering bore 911 on the spinous process. Preferably, arms 913, 914 are sized such they contact the lamina on either side of a vertebra to be reinforced. The distal ends 917, 918 of arms 913, 914 comprises lamina limit surfaces which contact the lamina of the vertebra to be treated limiting the depth to which guide 910 may be inserted over the spinous process. In this embodiment, arms 913, 914 are formed in one piece with connector section 912 and are joined to connector sections 912 by living hinges 915, 916. Living hinges 915, 916 allow arms 913, 914 to flex outwards as shown by the arrows and thus conform to the geometry of the spinous process while still centering bore 911 upon the apex of the spinous process. Guide 910 is preferably made of plastic.

FIG. 9C shows a U-shaped guide 920 having a bore 921 in connector section 922. Bore 921 acts as a position and direction guide for introduction of a needle or other surgical instrument. Guide 920 comprises two arms 923, 924 formed in one piece with connector section 922. Preferably, arms 923, 924 are sized such they contact the lamina on either side of a spinous process to be reinforced. Each arm 923, 924 comprises a finger 925, 926 which is displaced inwards relative to the arms 923, 924. The fingers 925, 926 are designed to engage the sides of the spinous process. The fingers are flexible, allowing the fingers to conform to the geometry of the spinous process while centering bore 921 on the apex of the spinous process. Guide 920 is preferably made of plastic or metal.

FIG. 9D shows a U-shaped guide 930 having a bore 931 in connector section 932. Bore 931 acts as a position and direction guide for introduction of a needle or other surgical instrument. Guide 930 comprises two arms 933, 934 formed in one piece with connector section 932. Preferably, arms 933, 934 are sized such they contact the lamina on either side of a spinous process to be reinforced, Each arm 933, 934 comprises two fingers 935, 936, 937, 938 which are displaced inwards relative to the arms 933, 934. Fingers 935, 936, 937 and 938 are designed to engage the sides of the spinous process. Fingers 935, 936, 937, 938 are flexible, allowing the fingers to conform to the geometry of the spinous process while centering bore 931 on the apex of the spinous process. Guide 930 is preferably made of plastic or metal.

FIG. 9E shows a cylindrical guide 940 having a bore 941 passing through the body of the guide. At one end of guide 940, a radius 942 is cut from the cylinder perpendicular to the long axis of the cylinder and intersecting the center of the bore that passes through the cylinder. Radius 942 is designed to engage the radius of the apex of the spinous process, thus centering bore 941 over the spinous process. FIG. 9F shows a sectional view of the guide 940 along the long axis illustrating the intersection of bore 941 with radius 942. Guide 940 is preferably made of plastic or metal.

FIG. 9G shows a two-component guide 950 having a bore 951 through connector section 952. Connector section 951 is generally cylindrical in shape and has a flange 955 disposed on one end. Flange 955 retains arms 953, 954 which are preferably formed of one piece of flexible material. The flexible material of arms 953 and 954 is designed to conform to the geometry of the spinous process thus centering bore 951 upon the spinous process. In an alternative (not shown) the flange 955 of connector section 951 forms a radius, as described with respect to FIG. 9E above, to better conform to the apex of the spinous process. Connector section of guide 950 is preferably made of a rigid metal or plastic whereas arms 953, 954 are preferably made of a soft flexible plastic or fabric material, such as TEFLON™, silicon rubber or latex rubber.

FIG. 9H shows a U-shaped guide 960 having a bore 961. Guide 960 comprises two arms 963, 964 which interlock a restraining collar 962. Restraining collar 962 comprises two channels 967, 968 which receive and retain a portion of each of arms 963, 964. Restraining collar 965 interlocks arms 963 and 964, but can slide with respect to the arms. Restraining collar 965 thus permits arms 963, 964 to flex in or out to conform to the sides of the spinous process. Restraining collar 962 also has a bore 965 designed to engage the spinous process. A needle or similar instrument passing through both bores will thus be centered on the spinous process. In an alternative (not shown) the restraining collar 962 forms a radius, as described with respect to FIG. 9E above, to better conform to the apex of the spinous process. FIGS. 9I and 9J show sectional views of guide 960 illustrating the interaction of arms 963, 964 and restraining collar 962. Guide 960 is preferably made of plastic or metal.

FIG. 9K shows a U-shaped guide 970 having a bore 971. Guide 970 comprises two arms 973, 974 which interlock a restraining collar 972. Restraining collar 972 comprises two channels 977, 978 which receive and retain a portion of each of arms 973, 974. Restraining collar 975 interlocks arms 973 and 974 but can slide vertically with respect to the arms. Restraining collar 972 thus forces arms 973, 974 to flex in or out to conform to the sides of the spinous process. Restraining collar 972 also has a bore 975. The vertical motion of restraining collar 972 with respect to arms 973, 974 constrains motion of bore 975 to the axis of bore 971. Thus, a needle or similar instrument passing through both bores 971, 975 will be centered on the apex of the spinous process. In an alternative (not shown) the restraining collar 972 forms a radius, as described with respect to FIG. 9E above, to better conform to the apex of the spinous process. FIGS. 9L and 9M show sectional views of guide 970 illustrating the interaction of arms 973, 974 and restraining collar 97. Guide 970 is preferably made of plastic or metal.

FIG. 9N shows a minimally-invasive guide 980. Guide 980 comprises centering guide 982 which has a bore 981 to receive a needle and a radiussed distal end 983 designed to engage spinous process 202. Centering guide 982 is disposed within a channel of depth guide 984. Centering guide 982 is connected to depth guide 984 by a spring 986 which allows relative motion of the centering guide and depth guide. Depth guide also has a bore 985 for receiving a needle. Bores 981 and 985 are aligned on an axis with the center of radius 983 such that, a needle or similar instrument passing through both bores 981, 985 will be centered on the spinous process. Depth guide 984 comprises depth gauge 988, which is preferably a small diameter stiff rod. Depth gauge 988 is designed to be inserted until the distal end 989 makes contact with lamina 210. Proximal surface 990 of depth guide 984 is at a fixed distance from distal end 989 and thus, proximal surface 990 can act as a limit to prevent needle insertion beyond the level of lamina 210. Guide 980 is used with an insertion device (such as shown in FIG. 6) having a limit surfaces designed to contact proximal surface 990 of the guide. The needle or wire, for example could be sized such that at maximum insertion it would be no deeper than the level of the lamina surface.

A primary purpose of the guide element is to center the bone cement injection instrument upon the apex of the spinous process and to guide insertion of the injection instrument along the axis of the spinous process. However, another purpose of the guide may be to control the flow and location of bone cement during injection. Bone cement may flow from the spinous process into the space between the spinous process and the guide through pores and fissures in the spinous process. A guide element may be provided with sealing elements and surfaces in order to direct and contain the flow of the bone cement.

Figure 10A:
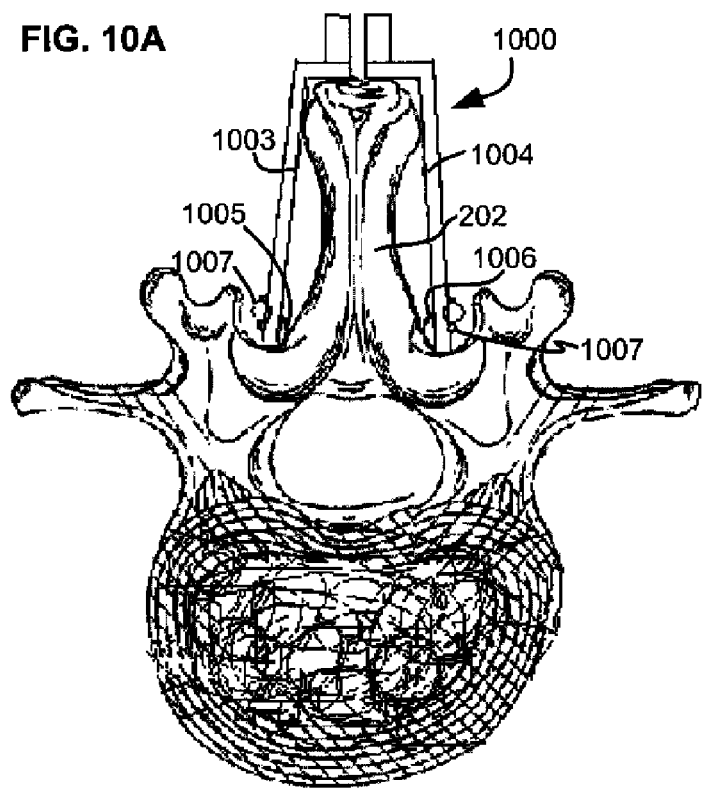
FIGS. 10A, 10B show a guide with sealing elements for controlling flow of bone filler.
Figure 10B:
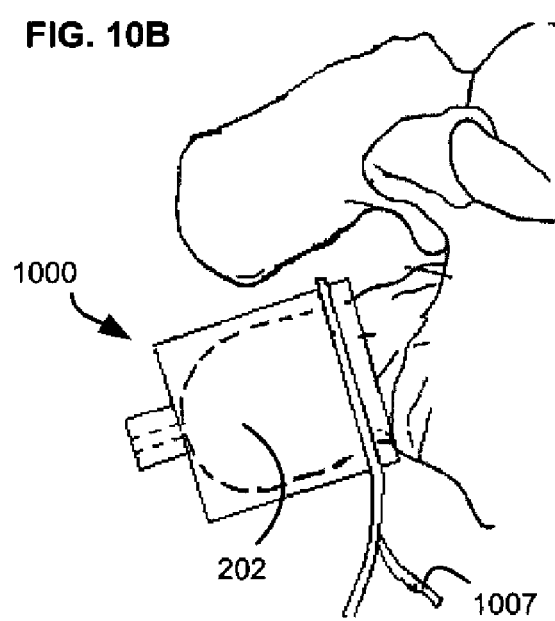

FIG. 10A shows a sectional view of guide 1000 positioned over spinous process 202. Each of arms 1003 and 1004 of guide 1000 is provided at the distal end with a sealing surface 1005, 1006. The sealing surface may be disposed on the distal portion of the arm where it contacts the spinous process or where it contacts the lamina or both. Sealing surfaces 1005, 1006 are preferably formed of a conformable polymer substance which readily conforms to the surface of the spinous process thus providing a temporary seal. A suitable seal may be formed using a soft latex rubber silicone rubber or similar materials. Sealing can be further aided by use of cord 1007 which goes around the spinous process and the two arms. Cinching cord 1007 pushes sealing surfaces 1005 and 1006 against spinous process 202 improving the quality of the seal. FIG. 10B shows a different view of guide 1000 over spinous process 202 to better illustrates the location of cord 1007.

In certain cases, it may be desirable to deposit bone cement around the spinous process in order to further strengthen the spinous process. In such cases, the guide may be used to control the location and shape of the bone cement surrounding the spinous process. In this procedure, the guide is placed over the spinous process and then sealed to the spinous process. A needle is then passed into the spinous process and bone cement injected. Bone cement injection is continued until all fissures in the spinous process have been filled and bone cement has filled any space between the spinous process and guide. To assist flow of bone cement from the spinous process into the area between the spinous process and guide, the sides of the spinous process may be perforated with a needle or similar instrument prior to location of the guide. The perforations allow the bone cement to flow into the space between the guide and the spinous process. After injection, the bone cement must then be allowed to cure, a process which takes from 6-12 minutes. The guide controls the one cement during curing and may be removed after the bone cement has hardened. To aid removal the guide may be coated with TEFLON™ or similar non-stick material.

Figure 11A:
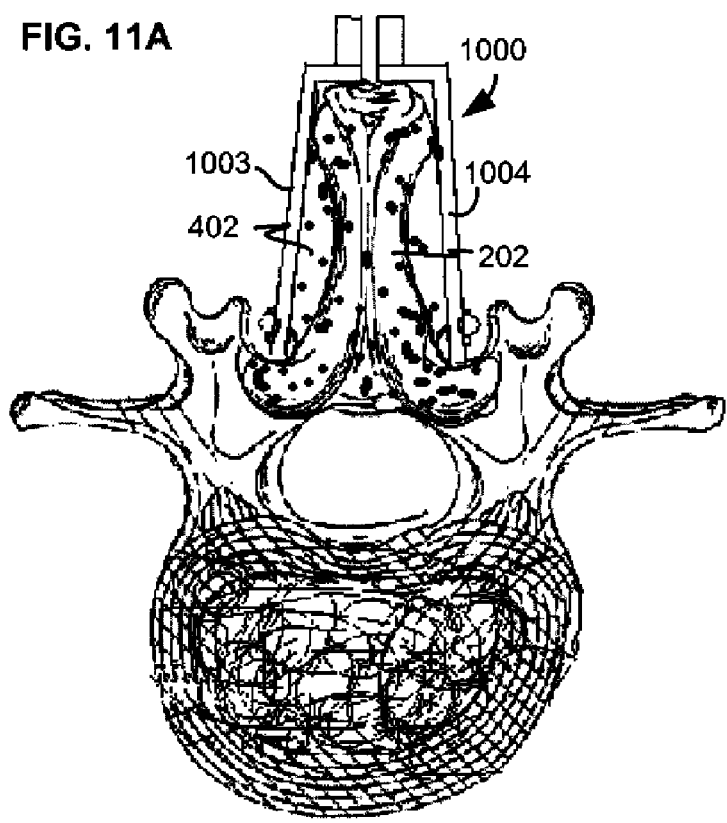
FIGS. 11A, 11B show operation of the guide of FIGS. 10A, 10B during injection of bone filler.
Figure 11B:
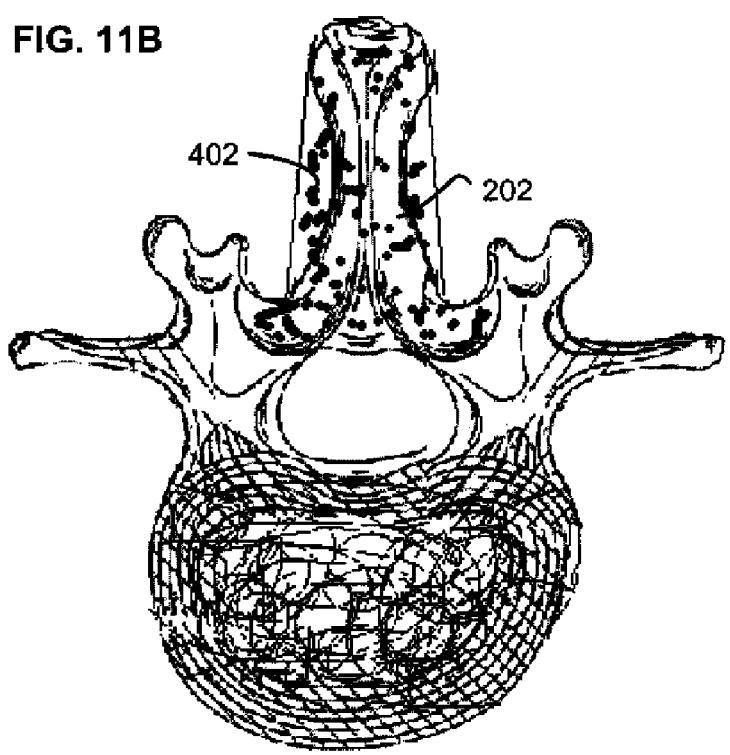

FIG. 11A illustrates injection of bone cement 402 into and around spinous process 202 utilizing the guide of FIGS. 10A and 10B. Bone cement 402 impregnates spinous process 202 and seeps into the void between guide 1000 and spinous process 202. Note that guide 1000 controls the flow of the bone cement. After the bone cement has hardened, the guide may be removed. As illustrated in FIG. 11B bone cement 402 retains its shape in and around spinous process 202 after removal of the guide.

Figure 12:
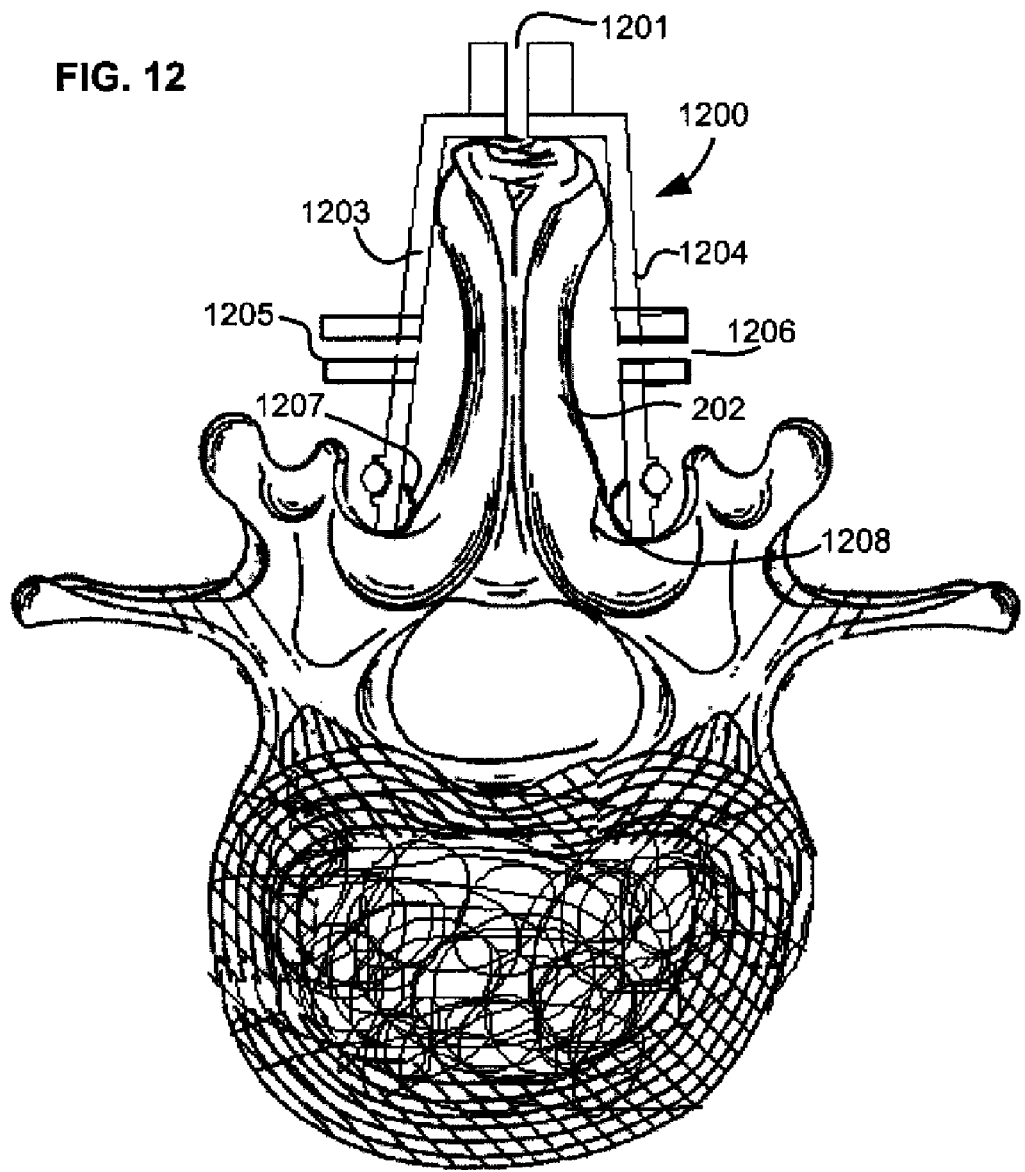
FIG. 12 shows an alternative guide in accordance with one embodiment of the invention comprising vacuum ports for enhancing flow of bone filler into the spinous process and lamina and providing additional bone cement injection sources.

FIG. 12 illustrates an alternative embodiment of the guide. As shown in FIG. 12, each of the arms 1203, 1204 of guide 1200 is provided with a port 1205, 206 which communicates with the space surrounding the spinous process. Each of ports 1205, 1206 may be attached to vacuum to aid injection of bone cement through bore 1201. Application of vacuum to port 1203 or port 1204 creates negative pressure in the spinous process and the space around the spinous process. The negative pressure serves to force arms 1203, 1204 and more particularly sealing surfaces 1207, 1208 against spinous process 202 making a better seal. The negative pressure also serves to encourage the bone cement to seep through and impregnate pores and fissures in the spinous process. After impregnation of spinous process 202 with bone cement, ports 1205, 1206 may optionally be used to inject bone cement into the space around the spinous process.

Figure 13A:
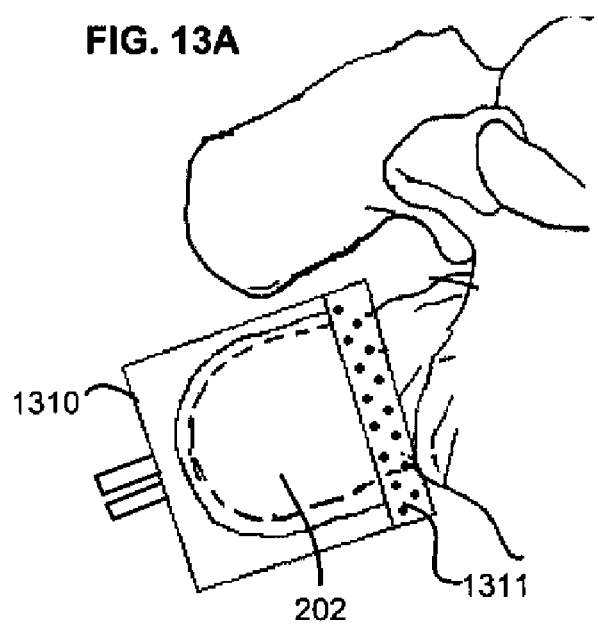
FIGS. 13A, 13B show alternative sealing elements for use with guides in accordance with embodiments of the invention.
Figure 13B:
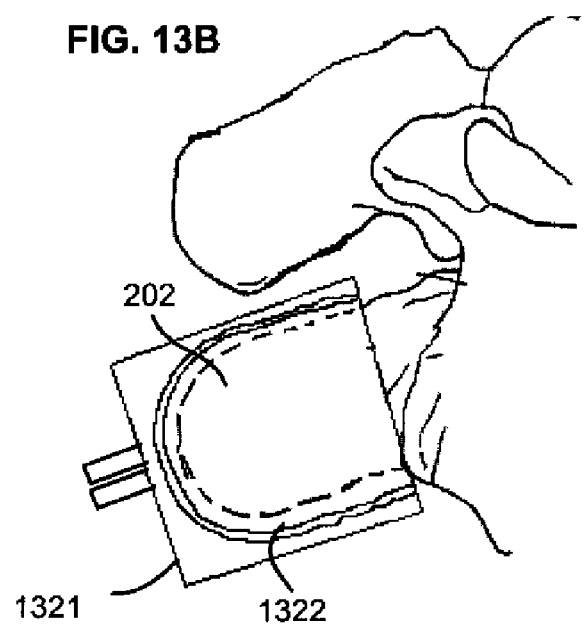

Various methods may be used to control the location and shape of bone cement. As illustrated in the guide of FIG. 10 sealing surfaces may be formed on the guide. Such sealing elements may comprise, for example inflatable elements attached to the guide that are forced into contact with the spinous process upon inflation. Alternatively, separate sealing elements may be placed over the spinous process prior to application of the guide. FIGS. 13A and B show two alternative sealing embodiments. As shown in FIG. 13A the guide 1310 may be sealed to the spinous process 202 using a conformable/tacky surface 1311 on the guides. In addition, as shown in FIG. 13B a polymer sealing material 1321 may be heat-sealed along line 1322 in place around the spinous process 202. These sealing surfaces may be part of the guide as previously described. However, alternatively, the sealing surface may be applied to a conformable polymer tape. The tape can be wrapped around the spinous process and then a guide may be placed over the spinous process and tape.

The methods described above may be used to strengthen the spinous process to guard against damage to the spinous process or repair trauma to the spinous process. However, as previously stated, the method of the present invention is particularly advantageous when utilized in combination with other interventions that interact with the spinous process. An example of such a procedure is the X-STOP™ procedure in which a spinous process distractor is inserted between the spinous processes of adjacent vertebrae as shown in FIG. 1. Distraction of the spinous processes serves to relieve problems caused by spinal stenosis. This procedure and implant is described in detail in U.S. Pat. No. 6,669,842 to Zucherman et al titled, "Spine Distraction Implantation" which is incorporated herein by reference. The method of the present invention may advantageously be used in combination with such a procedure to reinforce one or more spinous processes. This method will thus make interventions such as the X-STOP™ procedure available to a wider range of patients and enhance the outcome of such procedures.

In practice, the method of the present invention may be used to reinforce each spinous process that will be adjacent to the distractor. Thus, as shown in FIG. 1, bone cement may be injected into both spinous processes 102 and 103. To minimize the number of procedures and discomfort to the patient, the reinforcing procedure and distractor implant procedure may be performed in a single procedure, First, each spinous process is located and bone cement is injected as previously described. Next, the bone cement is allowed to harden, a process that typically takes from 6-12 minutes. Next, the distractor is implanted between the reinforced spinous processes as described in U.S. Pat. No. 6,669,842.

Although, the use of the invention has been described with respect to the X-STOP™ it will be apparent that the reinforcement of the spinous process would likewise be a useful part of any spinal intervention which interacts with the spinous process. Such procedures include for example procedures where implants are bolted to the spinous process or where screws are inserted into the spinous process or where distraction or fixation of spinous processes is performed.

A test was conducted to determine the effectiveness of the injection of bone cement to increase the strength of a spinous process. Eighteen vertebrae were procured and cleaned. The bone mineral density of each vertebra was then measured. The vertebrae were then grouped in adjacent pairs and one vertebra from each pair was randomly assigned to a test group, the remaining vertebrae were assigned to the control. The mean bone mineral density of the control group was $0.99 \pm 0.13$ g/cm$^2$ compared to the mean bone mineral density of the test group of $0.98 \pm 0.10$ g/cm$^2$.

Figure 14A:
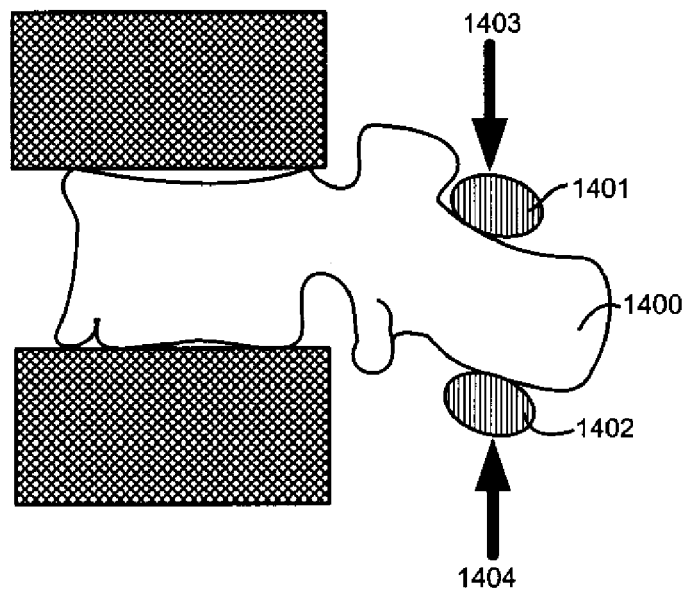
FIG. 14A illustrates a test performed to measure spinous process strength.
Figure 14B:
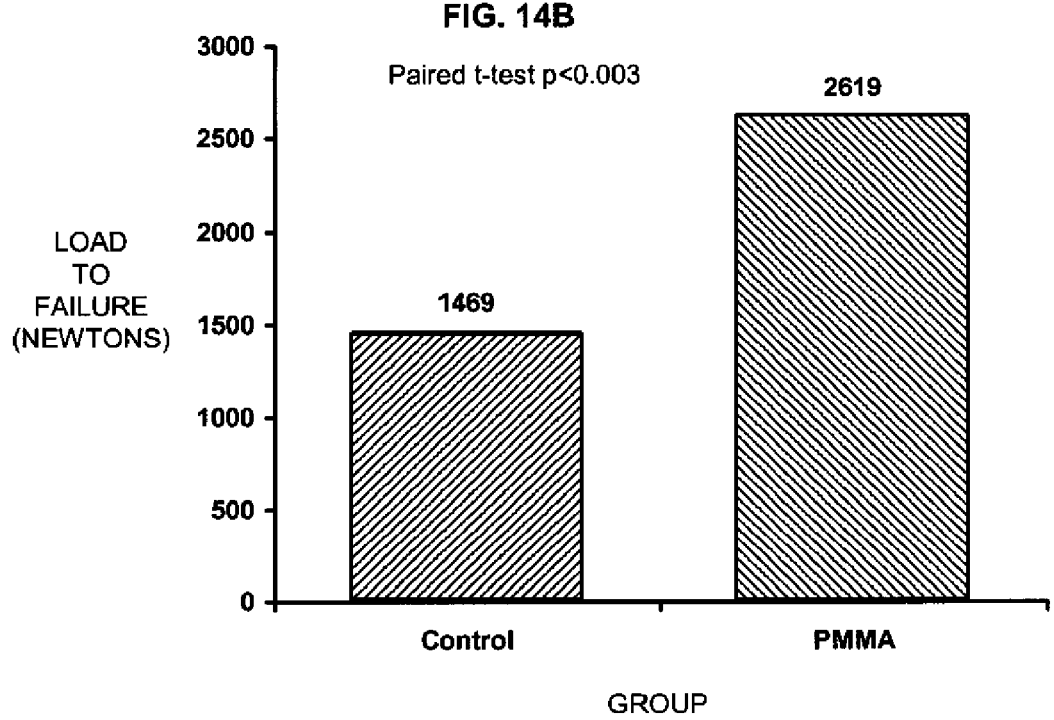
FIG. 14B is a table of the results of the test of FIG. 14A.

After scanning and assigning the specimens, bone cement (in this case PMMA) was then injected through an 11-gauge needle inserted into the spinous process of each vertebra in the test group. The mean volume of bone cement injection was $2.2 \pm 0.3$ cc. The bone cement was then allowed to cure. As shown in FIG. 14A, each of the test and control vertebra were then tested for strength by positioning a spinous process 1400 between two bars 1401, 1402 and loading the specimens as shown by arrows 1403, 1404 at 1 cm/min until failure. The results of the test were analyzed as shown in FIG. 14B. As shown in FIG. 14B, the test results showed that the strength of the spinous processes injected with PMMA was significantly higher than the strength of the un-reinforced control group. This preliminary data demonstrated that under the experimental conditions injection of bone cement into the spinous process could increase the strength of the spinous process of a vertebra by 78%.

The foregoing description of preferred embodiments of the present invention has been provided for the purposes of illustration and description. It is not intended to be exhaustive or to limit the invention to the precise forms disclosed. Many embodiments were chosen and described in order to best explain the principles of the invention and its practical application, thereby enabling others skilled in the art to understand the invention for various embodiments and with various modifications that are suited to the particular use contemplated. It is intended that the scope of the invention be defined by the claims and their equivalents.

We claim:

1. A method for strengthening a vertebra having a spinous process and a lamina wherein the method comprises:
   (a) positioning a guide such that at least a portion of a surface of the guide engages the vertebra whereby a guide bore of the guide is aligned with the spinous process;
   (b) inserting an injector through the guide bore into the spinous process and
   (c) flowing a reinforcing material through the injector into the spinous process.

2. The method of claim 1, wherein step (a) comprises positioning the guide relative to the spinous process such that a first surface of the guide engages the spinous process and the guide bore is aligned with the spinous process.

3. The method to claim 1 wherein step (a) comprises positioning the guide relative to the spinous process such that a first surface of the guide engages the spinous process, a second surface of the guide engages the lamina and the guide bore is aligned with the spinous process.

4. The method of claim 1, comprising the step of making a hole in a side of the spinous process prior to positioning the guide.

5. The method of claim 1, comprising the step of creating a cavity inside the spinous process by inserting a cavity-forming device through the guide bore into the spinous process prior to inserting the injector.

6. The method of claim 5, wherein the cavity-forming device is a surgical instrument selected from the group consisting of: wire, awl, drill, chisel, brush and inflatable body.

7. The method of claim 1, comprising the steps of inserting an inflatable device into the spinous process through the guide bore and inflating the inflatable body prior to inserting the injector.

8. The method of claim 1, wherein the injector has a stylet and wherein step (b) comprises:
    inserting an injector and stylet inside the injector through the guide bore into the spinous process and then removing the stylet.

9. The method of claim 1, wherein the reinforcing material is bone cement.

10. The method of claim 1, wherein the guide includes at least one port adapted to allow the injector to inject reinforcing material into a side of the spinous process.

11. The method of claim 1, wherein the guide includes at least one port adapted to allow the injector to inject reinforcing material adjacent to a side of the spinous process.

12. The method of claim 1, wherein the positioning step includes positioning the guide relative to the spinous process such that the surface includes first and second sides of the guide that are biased toward the spinous process.

13. The method of claim 1, wherein the surface of the guide includes first and second arms and a connector between the first and second arms and said guide bore positioned in the connector, and wherein the positioning step includes positioning the first and second arms against first and second sides of a spinous process, and positioning the connector adjacent to an apex of the spinous process.

14. A method for strengthening a vertebra having a spinous process, the method comprising the steps of:
    positioning a guide having first and second arms and a connector between the first and second arms adjacent to the spinous process with at least a portion of the first leg an at least a portion of the second leg biased against sides of the spinous process, and wherein the positioning step includes positioning a guide bore provided in the connector adjacent to an apex of the spinous process;
    inserting an injector through the guide bore into the spinous process; and
    injecting bone cement through the injector into the spinous process.

15. The method of claim 14, comprising the step of creating a cavity inside the spinous process by inserting a cavity-forming device through the guide bore into the spinous process prior to inserting the injector.

16. The method of claim 14, wherein the cavity-forming device is a surgical instrument selected from the group consisting of wire, awl, drill, chisels, brush and inflatable body.

17. The method of claim 14, wherein the injector has a stylet and wherein step (b) comprises:
    inserting an injector and stylet inside the injector through the guide bore into the spinous process and then removing the stylet.

18. The method of claim 14, comprising the step of making a hole in a side of the spinous process prior to positioning the guide.

19. method for strengthening a spinous process of a vertebra having a lamina wherein the method comprises:
    inserting a guide over the spinous process;
    inserting a surgical instrument having a bore through the guide into the spinous process; and
    forcing a flowable reinforcing material through the tubular bore such that it flows into the spinous process.

20. A guide for use in a procedure to introduce a surgical instrument having an insertion axis and a distal tip along a desired axis of a spinous process of a vertebra wherein the guide comprises:
    a first arm;
    a second arm;
    a connector positioned between the first arm and the second arm, at least one of the first arm and the second arm being flexibly coupled to the connector such that the first arm and the second arm are adapted to conform to the geometry of the spinous process;
    a guide bore adapted to allow passage of the surgical instrument; and
    wherein the guide bore is adapted to control the insertion axis of the instrument such that engagement of the spinous process by the first arm and the second arm aligns the insertion axis of the instrument with the desired axis of the spinous process.

21. The guide of claim 20
    wherein engagement of the spinous process is by a first surface of the first arm and a second surface of the second arm.

22. A guide for use in a procedure to introduce a surgical instrument having an insertion axis and a distal tip along a desired axis of a spinous process of a vertebra wherein the guide comprises:
    a guide surface adapted to engage the spinous process;
    a guide bore adapted to allow passage of the surgical instrument; and
    first and second arms;
    a connector positioned between the first and second arms;
    wherein the guide bore is adapted to control the insertion axis of the instrument such that engagement of the spinous process by the guide surface of the guide aligns the insertion axis of the instrument with the desired axis of the spinous process;
    wherein the guide surface adapted to engage the spinous process comprises a first surface of the first arm and a second surface of the second arm; and
    wherein at least one of the first surface and the second surface comprises a sealing element that is sufficiently compliant to conform to the surface of the spinous process to create a barrier to inhibit the flow of a fluid reinforcing material.

23. The guide of claim 20,
    wherein in a first configuration the first arm and second arm are spaced sufficiently far apart to allow the guide to be positioned over the apex of a spinous process and in a second configuration, the first arm and second arm are spaced sufficiently close together to be biased against the sides of the spinous process.

24. The guide of claim 20, wherein the guide further comprises:
    a collar;
    wherein a guide surface adapted to engage the spinous process comprises a first surface of the first arm and a second surface of the second arm;

and wherein the collar movably engages the first and second arms such that, in a first position of the collar, the first surface and second surface are spaced sufficiently, far apart to allow the guide to be positioned over the apex of a spinous process and, in a second position of the collar, the first surface and second surface are spaced sufficiently close together to be biased against the sides of the spinous process.

25. The guide of claim 20,
wherein at least one of the first arm and the second arm comprises a port for the introduction of a fluid reinforcing material between the guide and the spinous process.

26. The guide of claim 20, wherein the guide comprises a depth guide which controls a depth of insertion of a surgical instrument inserted through the guide bore.

27. The guide of claim 20, wherein the guide comprises a depth guide which comprises:

a depth gauge surface which contacts a surface of a lamina of the vertebra;
and a proximal surface;
and wherein the depth gauge surface and the proximal surface are at a fixed distance from each other so that the proximal surface engages the surgical instrument to prevent insertion of the distal tip of the surgical instrument beyond the lamina of the vertebra.

28. The guide of claim 20, wherein the guide comprises a depth guide;
wherein the guide surface adapted to engage the spinous process comprises a first surface of the first arm and a second surface of the second arm; and
wherein the depth guide is adapted to contact a lamina of the vertebra and limit insertion of the surgical instrument.

* * * * *